US010631890B2

(12) United States Patent
Palushi et al.

(10) Patent No.: US 10,631,890 B2
(45) Date of Patent: Apr. 28, 2020

(54) TISSUE SHAVING INSTRUMENT

(71) Applicant: Acclarent, Inc., Irvine, CA (US)

(72) Inventors: Jetmir Palushi, Irvine, CA (US); Fatemeh Akbarian, Rancho Palos Verdes, CA (US); Itzhak Fang, Irvine, CA (US); Don Q. Ngo-Chu, Irvine, CA (US); Henry F. Salazar, Pico Rivera, CA (US)

(73) Assignee: Acclarent, Inc., Irvine, CA (US)

( * ) Notice: Subject to any disclaimer, the term of this patent is extended or adjusted under 35 U.S.C. 154(b) by 184 days.

(21) Appl. No.: 15/795,473

(22) Filed: Oct. 27, 2017

(65) Prior Publication Data

US 2019/0125391 A1  May 2, 2019

(51) Int. Cl.

| A61B 17/32 | (2006.01) |
|---|---|
| A61B 17/16 | (2006.01) |
| A61B 17/00 | (2006.01) |
| A61B 17/22 | (2006.01) |
| A61B 17/24 | (2006.01) |

(52) U.S. Cl.
CPC .... *A61B 17/32002* (2013.01); *A61B 17/1688* (2013.01); *A61B 2017/00398* (2013.01); *A61B 2017/22079* (2013.01); *A61B 2017/246* (2013.01); *A61B 2017/320024* (2013.01); *A61B 2017/320032* (2013.01); *A61B 2217/005* (2013.01)

(58) Field of Classification Search
CPC .......... A61B 17/32002; A61B 17/1688; A61B 2017/00398; A61B 2017/22079; A61B 2017/246; A61B 2017/320024; A61B 2017/320032
See application file for complete search history.

(56) References Cited

U.S. PATENT DOCUMENTS

| 5,084,052 A * | 1/1992 | Jacobs .............. A61B 17/32002 |
|---|---|---|
| | | 606/170 |
| 5,730,752 A | 3/1998 | Alden et al. |
| 7,699,846 B2 | 4/2010 | Ryan |
| 8,109,956 B2 | 2/2012 | Shadeck |
| 8,574,254 B2 | 11/2013 | Hedstrom et al. |

(Continued)

OTHER PUBLICATIONS

U.S. Appl. No. 15/298,903, entitled "Multi-Window Surgical Cutting Apparatus," filed on Oct. 20, 2016.

(Continued)

*Primary Examiner* — Tuan V Nguyen
(74) *Attorney, Agent, or Firm* — Frost Brown Todd LLC (57) ABSTRACT

A surgical instrument and method of removing a portion of a tissue mass includes a shaft, a cutting member, and an aspiration vent. The shaft has a shaft lumen, a shaft window, and a shaft edge. The cutting member is disposed within the shaft lumen and is configured to cyclically move from a first position to a second position relative to the shaft. The cutting member includes a cutting window opening, a cutting edge, and a suction lumen to cut the tissue portion with the cutting member in the first position. The aspiration vent extends through at least one of the shaft or the cutting member for fluid communication with the suction lumen to suction an airflow for urging the tissue portion away from the cutting edge and along the suction lumen.

20 Claims, 9 Drawing Sheets

(56) References Cited

U.S. PATENT DOCUMENTS

| | | | |
|---|---|---|---|
| 2006/0200123 A1* | 9/2006 | Ryan | A61B 18/148 606/48 |
| 2008/0021488 A1* | 1/2008 | Berberich | A61B 17/32002 606/170 |
| 2012/0191116 A1* | 7/2012 | Flynn | A61B 10/0275 606/170 |
| 2015/0190163 A1 | 7/2015 | Ciulla et al. | |

OTHER PUBLICATIONS

Extended European Search Report dated Mar. 26, 2019 for Application No. 18202795.3, 9 pages.

* cited by examiner

TISSUE SHAVING INSTRUMENT

BACKGROUND

Surgical cutting instruments configured for removal of lesions, polyps and fibroids within the nasal cavity are known. Some configurations may include an elongated inner member rotatably coaxially disposed within a tubular outer member. The distal end of the outer member includes an opening, and the distal end of the inner member includes cutting edges. The proximal ends of the two members may be connected to a handle directly or via a detachable hub. The inner member may be hollow and in communication with an aspiration port so that severed tissue, etc. can be aspirated out through the hollow member. The cutting edges can have any various configurations suitable for the particular type of tissue or bone cutting to be done, with the opening configured to cooperate with the specific cutting edge configuration.

To use such surgical cutting instrument to address tissue or bone, the opening/cutting edge is advanced to the target surgical site, and the opening positioned adjacent the tissue or bone to be removed. The opening may be repositioned to address tissue which was could not be accessed with the instrument in the previous position. Surgical cutting instruments with a fixed opening allow surgeons to cut only in the direction of the fixed opening cutting. To access, cut and remove tissue at various locations, surgeons have to reposition the instrument at various angles; or in some instances, change to other instruments having a more appropriately arranged opening.

It may be desirable to access, cut and remove tissue and bone at various locations without having to reposition or change the surgical instrument. While several different surgical instruments and methods of use have been made for tissue and bone removal within the nasal cavity, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "front" and "rear" also are used herein for reference to relative positions. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Surgical Cutting Instrument

Figure 1:
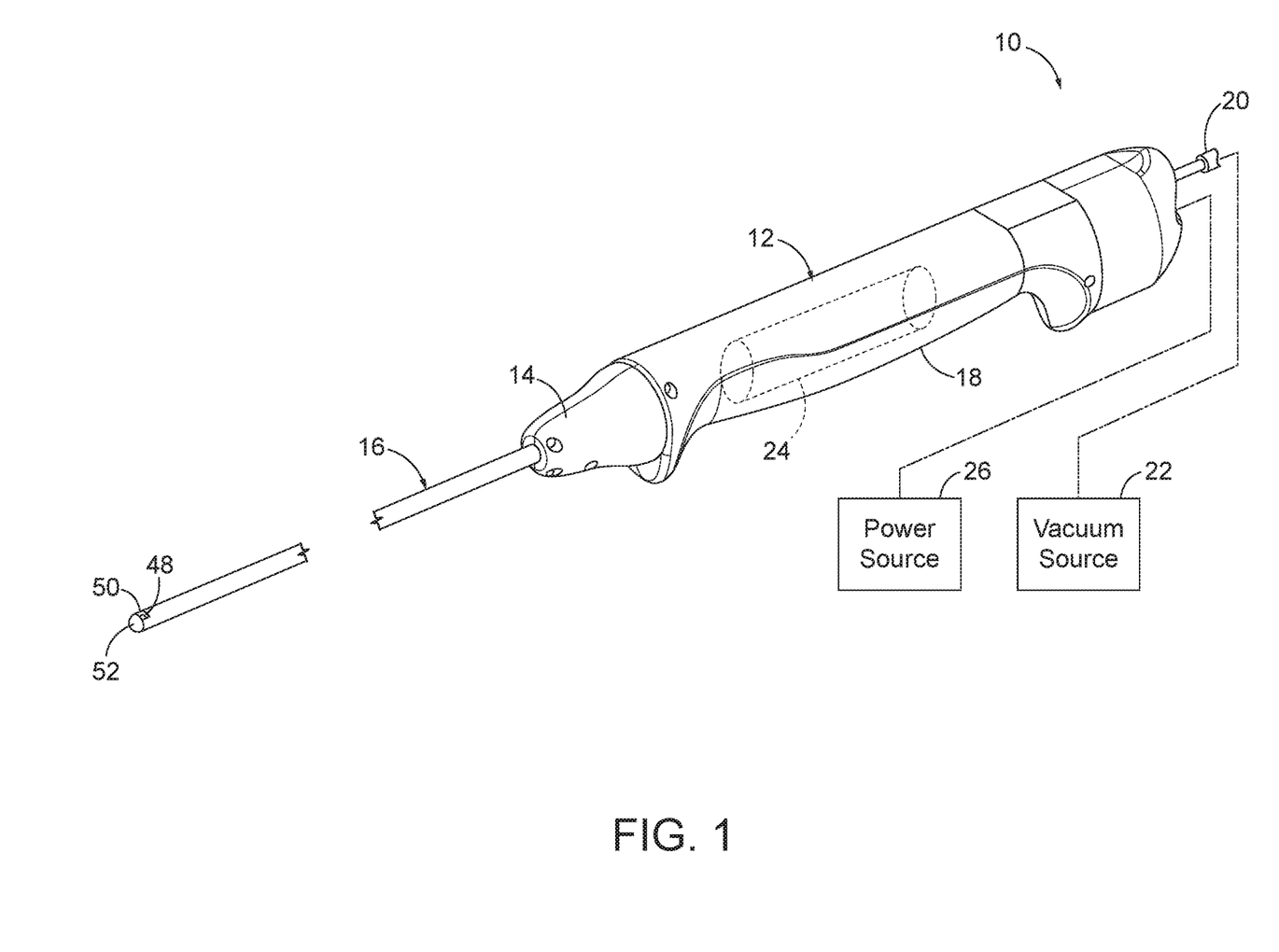
FIG. 1 depicts a perspective view of an exemplary surgical cutting instrument having a handle assembly and a first shaft assembly with a plurality of cutting window openings.

FIG. 1 shows an exemplary surgical cutting instrument (10) that may be used to remove tissue and bone from the nasal cavity, as well as from any other suitable location. Surgical cutting instrument (10) of the present example includes a handle assembly (12), a hub (14), and a shaft assembly (16) extending distally from handle assembly (12). Handle assembly (12) has a handle (18) which may be of any suitable configuration. Handle (18) may include controls for the operation of surgical cutting instrument (10), or the controls may be located remotely. Surgical cutting instrument (10) further includes a suction port (20) operatively connected to a vacuum source (22) and configured to enable aspiration of a tissue (23) (see FIG. 4A), such as a bone tissue, from a surgical site. Rotational motion is delivered by a motorized drive assembly (24) within handle assembly (12) to shaft assembly (16) in the present example, although any suitable rotational or oscillatory motion source may be utilized. For example, such motion source may be housed within handle assembly (12) or may be external and connectable to handle assembly (12). A power source (26) connects to motorized drive assembly (24) to power surgical cutting instrument (10) for use. In addition or alternatively, handle assembly (12) may house a battery (not shown).

Figure 2:
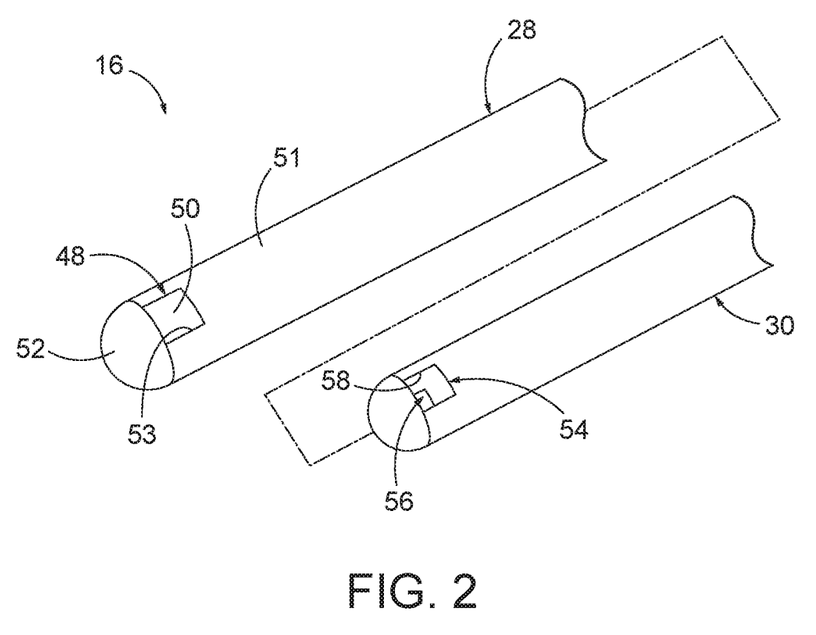
FIG. 2 depicts an exploded perspective fragmentary view of the shaft assembly of FIG. 1 having a shaft and a cutting member with the cutting window openings.
Figure 4A:
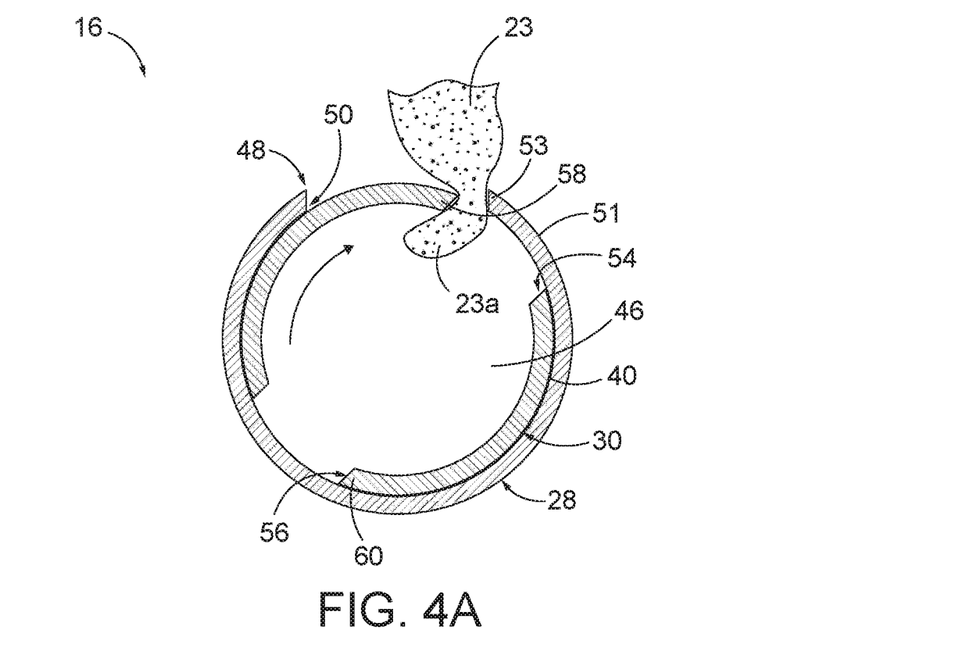
FIG. 4A depicts a sectional view of the shaft assembly of FIG. 1 taken transversely through the centerline and the cutting window openings, with various components hidden for clarity, illustrating a tissue extending through a window opening and against a cutting edge.
Figure 5:
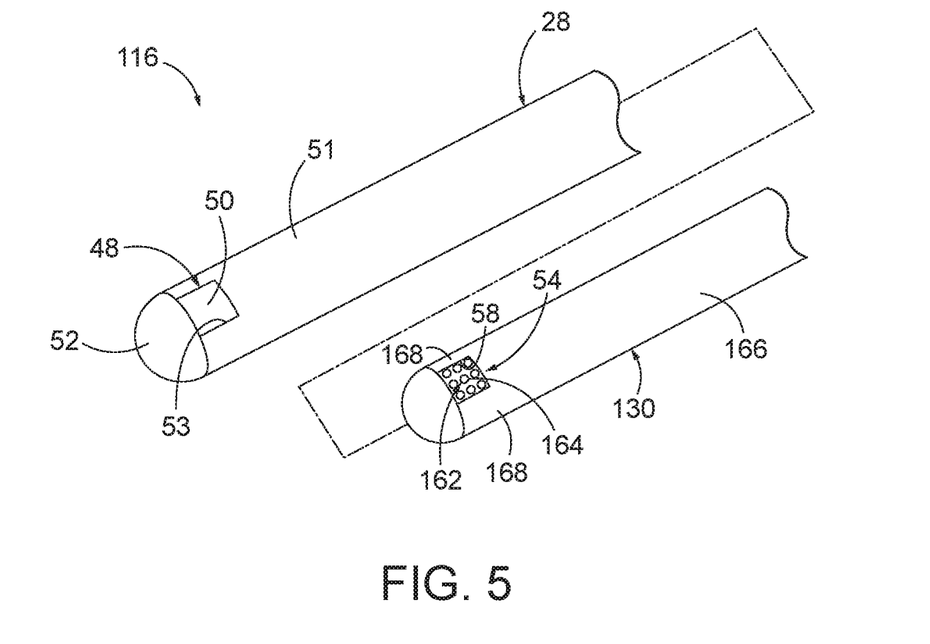
FIG. 5 depicts an exploded perspective fragmentary view of a second shaft assembly for use with the handle assembly of FIG. 1 having a shaft and a cutting member with a first exemplary aspiration vent.
Figure 10:
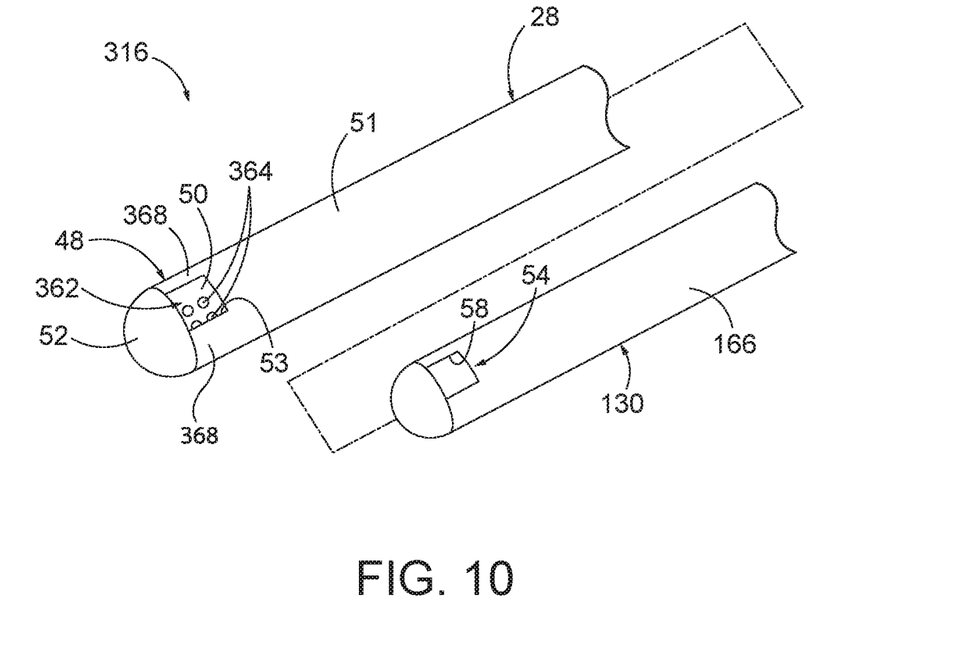
FIG. 10 depicts an exploded perspective fragmentary view of a third shaft assembly for use with the handle assembly of FIG. 1 having a shaft and a cutting member with a third exemplary aspiration vent.

FIG. 2 shows shaft assembly (16) in greater detail whereas FIGS. 5 and 10 show alternative shaft assemblies (116, 316) discussed below in greater detail. Each shaft assembly (16, 116, 316) generally includes an outer shaft (28) and an inner cutting member (30) collectively configured to receive and remove tissue (23) (see FIG. 4A) from the surgical site. Specifically, cutting member (30) is cyclically driven relative to outer shaft (28), such as by relative rotation, for such removal of tissue (23) (see FIG. 4A). Once removed, vacuum source (22) clears the removed tissue (23) (see FIG. 4A) via suction from cutting member (30) for removal of additional tissue (23) as desired. In one example discussed below, shaft assembly (16) has a plurality of cutting window openings (54, 56) with respective cutting edges (58, 60) to perform multiple tissue resections for removal per cycle. Thereby, shaft assembly (16) may remove tissue (23) (see FIG. 4A) more quickly and/or cycle speed of shaft assembly (16) may be reduced for various performance improvements. In addition to outer shaft (28) and cutting member (30) shaft assemblies (16, 116, 316) may also include a shield member (not shown) for selective tissue removal as described in U.S. patent application Ser. No. 15/298,903, entitled "Multi-Window Surgical Cutting Apparatus," filed Oct. 20, 2016, issued as U.S. Pat. No. 10,271,871 on Apr. 30, 2019, the disclosure of which is incorporated by reference herein.

Shaft assemblies (116, 316) further enhance tissue suction with one or more such cutting window openings (54, 56) via an aspiration vent (162, 262, 362, 462). Aspiration vents (162, 262, 362, 462) are configured to increase air flow, intermittently or continuously, through cutting member (30) for effectively clearing removed tissue (23) (see FIG. 4A) to increase tissue cutting capacity and/or decrease the likelihood of clogging cutting member (30) with tissue (23) during use. The following describes a variety of openings (164, 264, 364, 464) that singularly or collectively define aspiration vents (162, 262, 362, 462) for such use. Such openings (164, 264, 364, 464) may thus be dedicated solely to such venting or provide for venting and additional material flow as described herein. Openings (164, 264, 364, 464) discussed below may also be used in any combination together or with other features of surgical cutting instrument (10). The invention is thus not intended to be unnecessarily limited to the particular arrangement of openings (164, 264, 364, 464) for aspiration vents (162, 262, 362, 462). One or more alternative openings may thus be similarly configured as an alternative aspiration vent in accordance with the invention described herein. In any case, like numbers provided with respect to various shaft assemblies (16, 116, 316) indicate like features discussed herein.

A. Shaft Assembly with a Plurality of Cutting Window Openings

Figure 3:
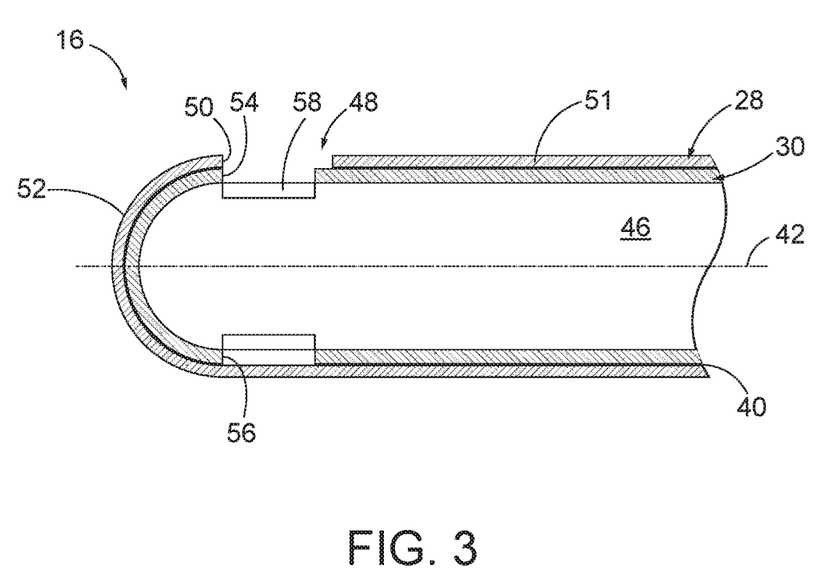
FIG. 3 depicts a cross-sectional view of the shaft assembly of FIG. 1 taken along a centerline thereof.

With respect to FIGS. 1-3, shaft assembly (16) has cutting member (30), which is illustrated as a tube, disposed within a longitudinally extending lumen (32) of shaft (28). Cutting member (30) is configured to be rotated about a longitudinal axis (42) of shaft assembly (16) at a distal portion. Although shaft assembly (16) is depicted as rigid, all or a portion of shaft assembly (16) may be flexible, with longitudinal axis (42) comprising a series of cross-sectional centers. Cutting member (30) defines a lumen (46) and extends proximally to handle assembly (12) and connects to motorized drive assembly (24), which rotatably drives cutting member (30) relative to shaft (28). In the present example, shaft (28) is formed of polycarbonate and cutting member (30) is formed of stainless steel. Of course, shaft (28) and cutting member (30) may be formed of one or more alternative materials in accordance with the invention described herein. The invention is thus not intended to be unnecessarily limited to manufacture with polycarbonate and stainless steel. While the present example of cutting member (30) is a hollow tube, cutting member (30) is not limited to being tubular and defining its own lumen (32). Cutting member (30) may be of any suitable configuration to provide one or more cutting edges (58, 60) and one or more openings (54, 56) in communication with vacuum source (22).

Shaft (28) includes a window region (48) having a shaft window opening (50) at distal portion. Distal portion includes a tubular sidewall (51) that distally terminates in a curved end, such as a generally hemispherical end (52). Shaft window opening (50) extends through tubular sidewall (51) of shaft (28) into central lumen (40) and is in fluid communication with the environment surrounding shaft (28). Shaft window opening (50) faces radially outward relative to longitudinal axis (42) such that tissue (23) (see FIG. 4A) is configured to be radially received through shaft window opening (50) into central lumen (40) in a radially inward direction. Shaft window opening (50) is surrounded by a relatively dull edge (53).

Figure 4B:
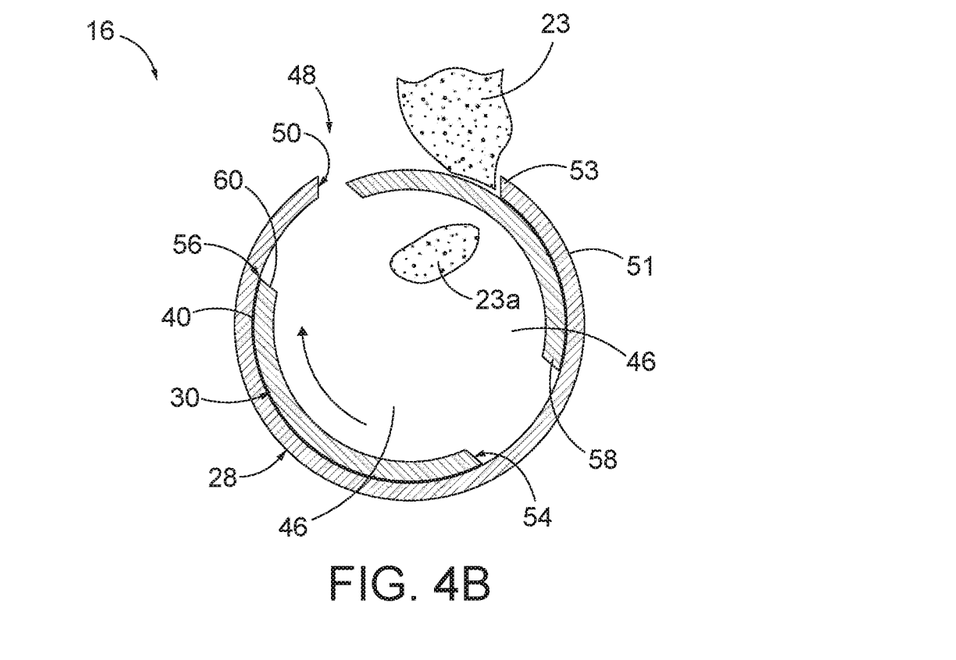
FIG. 4B depicts the sectional view of the shaft assembly similar to FIG. 4A, but showing the cutting edge rotating relative to the window opening and cutting the tissue while maintaining a vacuum for proximally clearing the tissue from the shaft assembly.

Cutting member (30) includes a front cutting window opening (54) and a rear cutting window opening (56) at distal portion of cutting member (30). Each cutting window opening (54, 56) is configured to longitudinally align with shaft window opening (50) and respectively includes a front cutting edge (58) and a rear cutting edge (60) (see FIG. 4A) extending therealong. It is noted that less than the entirety of front and rear cutting edges (58, 60) (see FIG. 4A) may be configured for cutting tissue (23) (see FIG. 4A) against an opposing edge (53) of shaft (28). As shown in FIGS. 2-4A, at least a portion of each of front and rear cutting edges (58, 60) are disposed to move adjacent to and across at least a portion of window region (48) when cutting member (30) is rotated or oscillated about longitudinal axis (42). FIG. 4A illustrates tissue (23) extending through shaft window opening (50), such as would occur when distal portion is urged radially against such tissue. As cutting member (30) moves in a clockwise direction, edge (53) of window region (48) provides an opposing surface to front cutting edge (58) whereby tissue (23) may be severed to remove a cut tissue portion (23a) therefrom as shown in FIG. 4B. Each of front cutting edge (58) and edge (53) may have any configuration which suitably cooperates with the other to sever tissue (23), such as a knife edge, a serrated edge, bipolar, monopolar or harmonic energy modality, or laser activated cutting edge.

The extent of movement and position of front cutting edge (58) relative to edge (53) is sufficient to separate tissue (23), whether by severing, tearing or any other mechanism. For example, front cutting edge (58) may cyclically move across at least a portion of window region (48). Further clockwise movement of cutting member (30) will advance front cutting edge (58) past edge (53), such as results from oscillation about longitudinal axis (42) or from full rotation about longitudinal axis (42). In the present example, cutting member (30) rotates clockwise to radially align rear cutting window opening (56) of cutting member (30) with shaft window opening (50) of shaft (28) to also receive and remove tissue (23) with rear cutting edge (60). Rear cutting edge (60) thereby severs tissue (23) against edge (53) as discussed above with respect to front cutting edge (58).

Referring back to FIG. 1 with further reference to FIGS. 3-4B, vacuum source (22) generates suction in a proximal direction along longitudinal axis (42) toward suction port (20). Without tissue (23) blocking cutting window openings (54, 56), such suction proximally withdraws a window airflow therethrough along lumen (46). However, once tissue (23) is respectively introduced into window openings (54, 56), suction effectively draws tissue (23) into the respective window opening (54, 56) for resection while tissue (23) blocks airflow along lumen (46). Airflow through lumen (46) essentially terminates such that vacuum source (22) accumulates the vacuum within lumen (46). Such termination of airflow may generally be referred to as a stalled airflow within lumen (46).

In use, with respect to FIG. 4A, tissue portion (23a) is cut from tissue (23) between front cutting edge (58) and dull edge (53) as front cutting window opening (54) rotatably passes by shaft window opening (50) and airflow stalls within lumen (46) while blocked by tissue (23). Cutting member (30) continues to cyclically rotate with tissue portion (23a) within lumen (46), such as shown in FIG. 4B. As rear cutting window opening (56) fluidly connects to shaft window opening (50), suction draws tissue (23) into rear cutting window opening (56) and another tissue portion (23a) is cut from tissue (23) between rear cutting edge (60) and dull edge (53) and rear cutting window opening (56). Thereby, two tissue portions (23a) are cut from the mass of tissue (23) for each revolution of cutting member (30) within outer shaft (28).

Generally, cycling cutting member (30) within outer shaft (28) creates friction therebetween that generates heat, vibration, and a reactionary torque in use and tends to wear shaft assembly (16), which affect performance and the useful life of shaft assembly (16). In the present example, shaft assembly (16) with two cutting window openings (54, 56) unidirectionally driven at 3,000 revolutions per minute (RPM) may resect up to 6,000 tissue portions (23a) per minute. In contrast, an alternative shaft assembly (not shown) having only one such cutting window opening would need to be driven faster at 6,000 RPM for resecting up to 6,000 tissue portions (23a). Lower speeds with two cutting window openings (54, 56) compared to higher speeds with one cutting thus comparatively reduce such heat, vibration, and torque generated by friction while maintaining similar tissue resection capabilities. Additional cutting window openings may be incorporated into alternative shaft assemblies (not shown) to increase tissue resecting capability per revolution for even further reducing drive speed of shaft assembly (not shown) as desired. The invention is thus not intended to be unnecessarily limited to one or two cutting window openings (54, 56). It will be appreciated that such performance benefits similarly apply to bidirectional oscillation of cutting member (30) within outer shaft (28) such that the invention is also not intended to be unnecessarily limited to unidirectional rotation.

B. Shaft Assembly and Aspiration Vent with a Plurality of Vent Openings Associated with an Inner Cutting Tube FIGS. 5-8B illustrate a shaft assembly (116) for use with handle assembly (12) (see FIG. 1) of surgical instrument (10) (see FIG. 1) that includes outer shaft (28), an inner cutting member (130), and window region (48) for cutting tissue (23) (see FIG. 9A) as discussed above. However, in contrast with shaft assembly (16) (see FIG. 2), shaft assembly (116) includes a first exemplary aspiration vent (162) configured to fluidly connect lumen (46) with the environment to suction a vented airflow along lumen (46) and urge tissue portion (23a) (see FIG. 9A) away from cutting window opening (54). Cutting member (130) is also similar to cutting member (30) (see FIG. 2) in most respects, but does not include rear cutting window opening (56) (see FIG. 2) with rear cutting edge (60) (see FIG. 2) in the present example. It will be appreciated that additional cutting window openings with cutting edges may be included with aspiration vent (162) in alternative examples and are thus not intended to be mutually exclusive. By way of example, additional cutting window openings may be positioned at alternative angles about shaft assembly (116) to incorporate aspiration vent (162) therebetween for use.

Figure 6:
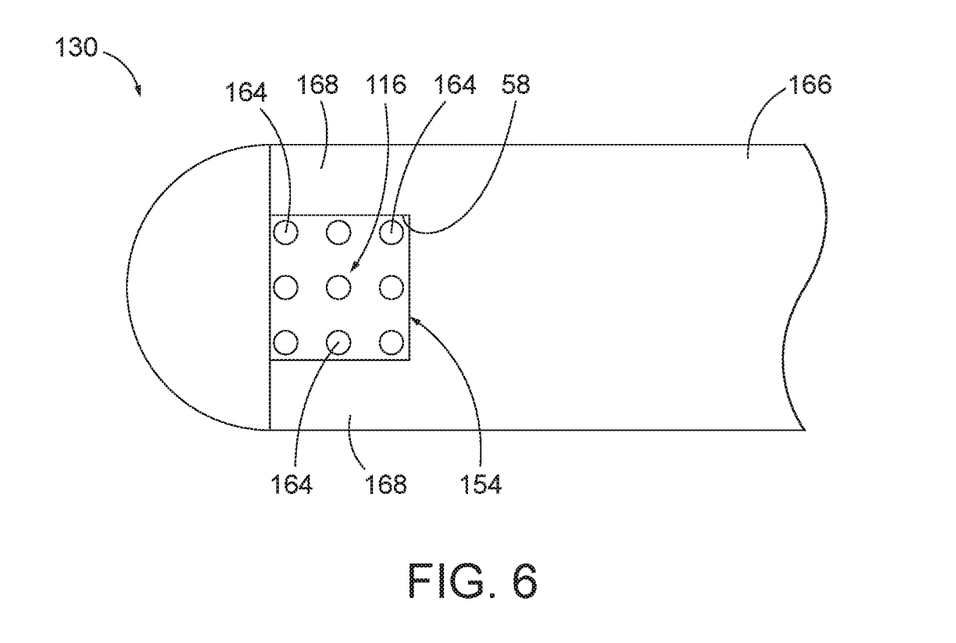
FIG. 6 depicts an enlarged front side elevational view of the cutting member of FIG. 5.
Figure 7:
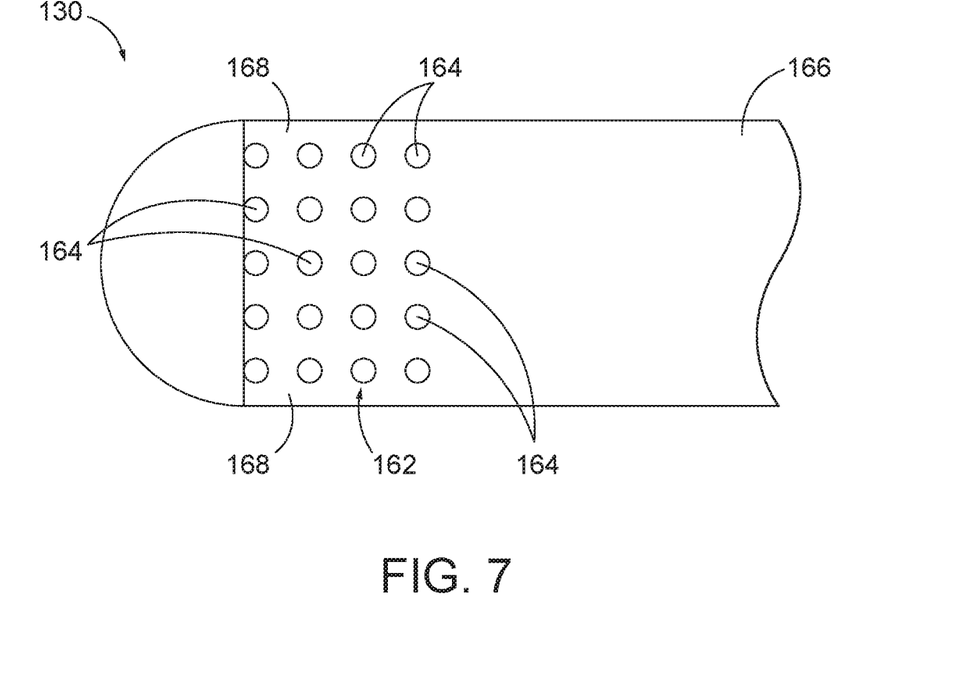
FIG. 7 depicts an enlarged rear side elevational view of the cutting member of FIG. 5.

With respect to FIGS. 5-7, aspiration vent (162) more particularly includes a plurality of vent openings (164) that are positioned opposite from cutting window opening (54) and extend through a tubular sidewall (166) of cutting member (130). Vent openings (164) of the present example are arranged in a series of rows and a series of columns. As oriented in FIGS. 6-7, vent openings (164) are circular bores arranged in five rows and four columns, although it will be appreciated that vent openings (164) may be alternatively sized and positioned. The columns of vent openings (164)

are offset from cutting window opening (54) to define a radial sidewall portion (168) on each radial side of cutting window opening (54). Each radial sidewall portion (168) is generally larger than shaft window opening (50) through shaft (28) such that alignment of radial sidewall portion (168) blocks airflow therethrough and fluidly disconnects the environment from lumen (46).

Figure 8A:
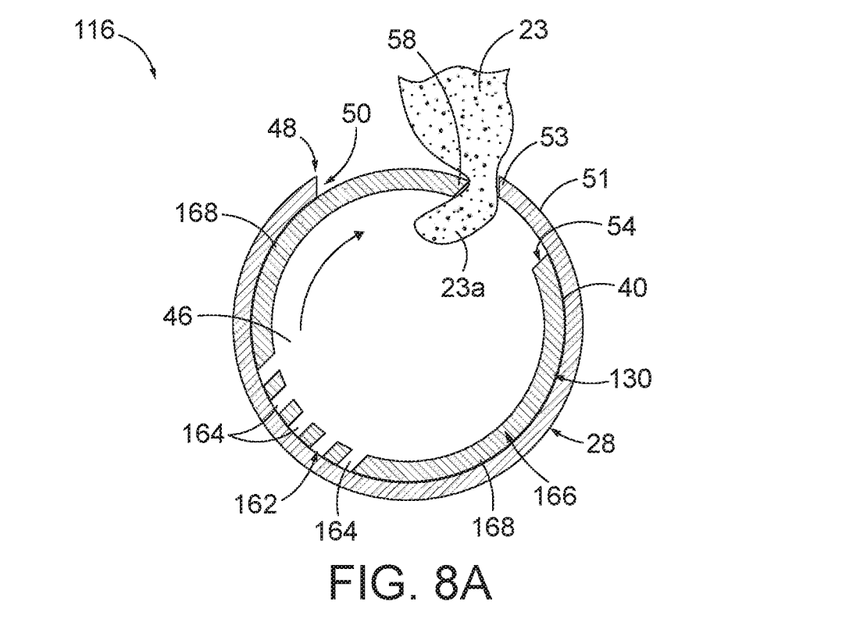
FIG. 8A depicts a sectional view of the shaft assembly of FIG. 5 taken transversely through the centerline and the aspiration vent, with various components hidden for clarity, illustrating a tissue extending through a window opening and against a cutting edge.
Figure 8B:
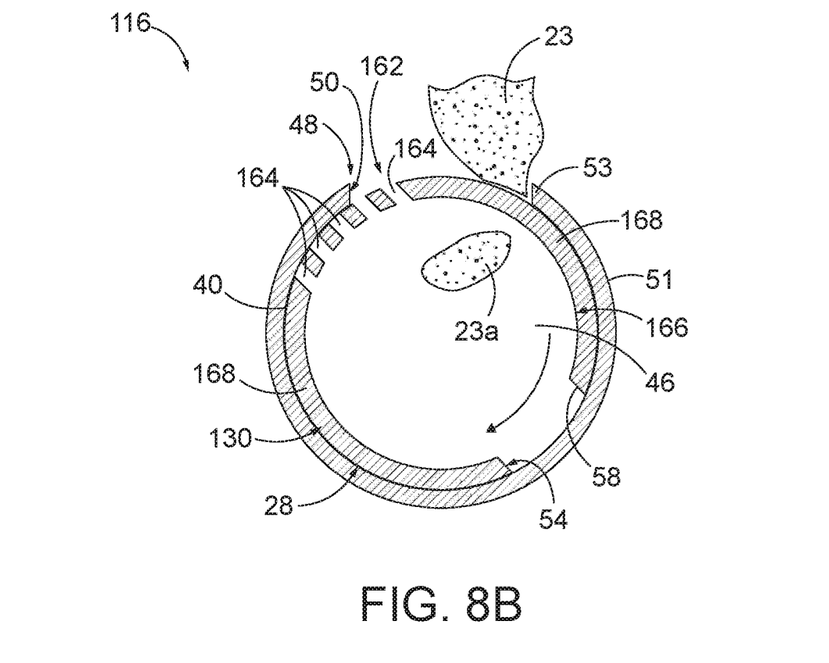
FIG. 8B depicts the sectional view of the shaft assembly similar to FIG. 8A, but showing the cutting edge rotating relative to the window opening and cutting the tissue while maintaining a vacuum for proximally clearing the tissue from the shaft assembly.

Cutting window opening (54) and vent openings (164) respectively cooperate with shaft window opening (50) through shaft (28) to intermittently suction a stalled airflow and a vent airflow along lumen (46) as shown in FIGS. 8A-8B. To this end, cutting edge (58) cuts tissue portion (23A) and vacuum source (22) (see FIG. 1) suctions tissue (23) into cutting window opening (54) as illustrated in FIG. 8A in the present example. Further cyclical rotation of cutting member (130) within shaft (28) causes vent openings (164) to align with shaft window opening (50) through another range of cyclical rotational positions for fluid communication therethrough. Vent openings (164) and shaft window opening (50) thus fluidly connect lumen (46) to the environment as aspiration vent (162) such that vacuum source (22) withdraws the vent airflow therethrough proximally along lumen (46). The vent airflow continues until each vent opening (164) rotates past shaft window opening (50) beyond alignment to fluidly disconnect lumen (46) from the environment. Thereby, vent airflow through lumen (46) essentially terminates as radial sidewall portion (168) covers shaft window opening (50) such that vacuum source (22) (see FIG. 1) accumulates the vacuum within lumen (46) and stalls airflow. As described herein, fluid disconnection of various openings and termination of airflow may not be complete disconnection and termination as some leakage may remain. Stalled airflow may thus result in a leakage airflow in some examples, but, in any case, such stalled airflow is less than the principle airflow through aspiration vent (162). The invention is thus not intended to be unnecessarily limited to complete disconnection of openings for full termination of airflow.

In use, with respect to FIG. 8A, tissue portion (23a) is cut from tissue (23) between front cutting edge (58) and dull edge (53) as cutting window opening (54) rotatably passes by shaft window opening (50) and stalls airflow within lumen (46). Cutting member (30) continues to cyclically rotate with tissue portion (23a) within lumen (46), such as shown in FIG. 8B. As vent openings (164) fluidly connect to shaft window opening (50) to collectively define aspiration vent (162), vacuum source (22) (see FIG. 1) draws vent airflow therethrough from the environment and into lumen (46). Vent airflow from aspiration vent (162) proximally flows toward suction port (20) (see FIG. 1) and, in turn, similarly urges tissue portion (23a) within lumen (46) away from cutting edge (58) and toward suction port (20). Vent airflow continues to proximally urge tissue portion (23a) clear of cutting edge (58) until vent openings (164) rotate past shaft window opening (50) to again stall airflow as shown again in FIG. 8A. The cyclical rotation of cutting member (30) within shaft (28) repeats the above cutting of tissue (23) and suctioning of intermittent window and vent airflows to effectively clear cutting edge (58) of tissue portions (23a).

Figure 9:
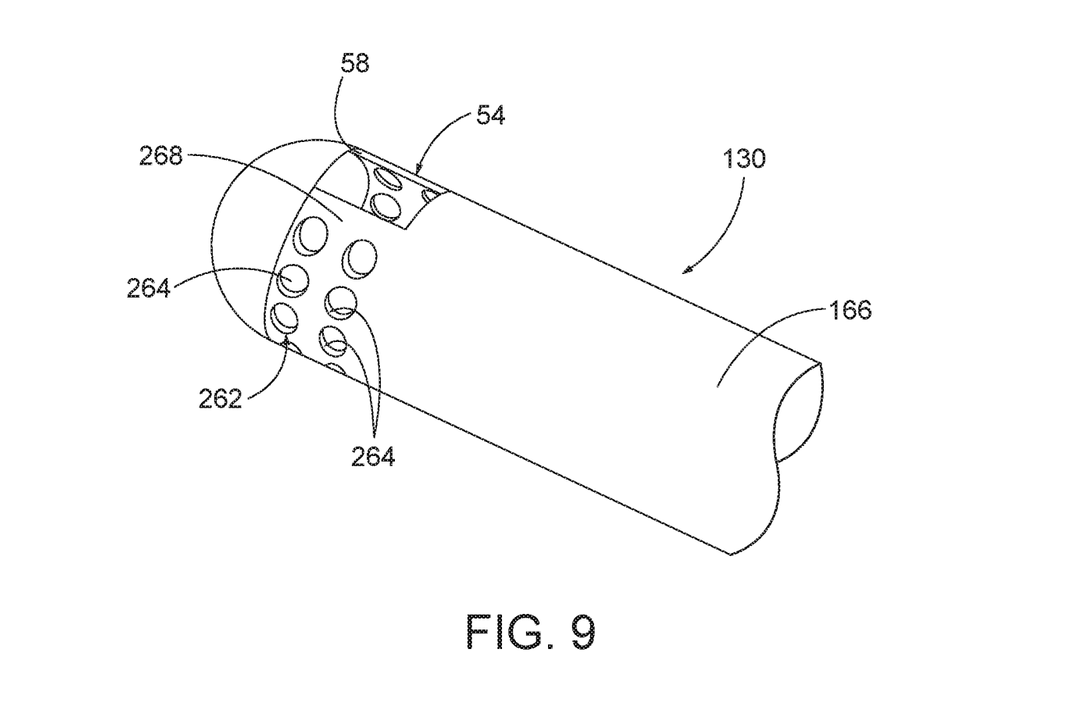
FIG. 9 depicts an exploded perspective fragmentary view of a cutting member similar to the cutting member of FIG. 5, but having a second exemplary aspiration vent.

FIG. 9 illustrates cutting member (130) with a second exemplary aspiration vent (262) having a plurality of vent openings (264). Aspiration vent (262) is similar to aspiration vent (162) (see FIG. 5) discussed above, but with vent openings (264) sized and positioned such that alternative radial sidewall portions (268) are generally smaller than shaft window opening (50). Thus, at least one of cutting window opening (54) and vent openings (264) are always in fluid communication with shaft window opening (50) for continuous window and/or vent airflows during cyclical movement rather than intermittent window and vent airflows as discussed above. Such vent openings (264) are thereby configured to reduce or even prevent, stalled airflow through lumen (46) during use.

C. Shaft Assembly and Aspiration Vent with a Plurality of Vent Openings Associated with an Outer Shaft FIGS. 10-13B illustrate a shaft assembly (316) for use with handle assembly (12) (see FIG. 1) of surgical instrument (10) (see FIG. 1) that includes outer shaft (28), inner cutting member (130), and window region (48) for cutting tissue (23) (see FIG. 9A) as discussed above. However, in contrast with shaft assemblies (16, 116) (see FIG. 2 and FIG. 5), shaft assembly (316) includes a third exemplary aspiration vent (362) configured to fluidly connect lumen (46) with the environment to suction a vented airflow along lumen (46) and urge tissue portion (23a) (see FIG. 13A) away from cutting window opening (54).

Figure 11:
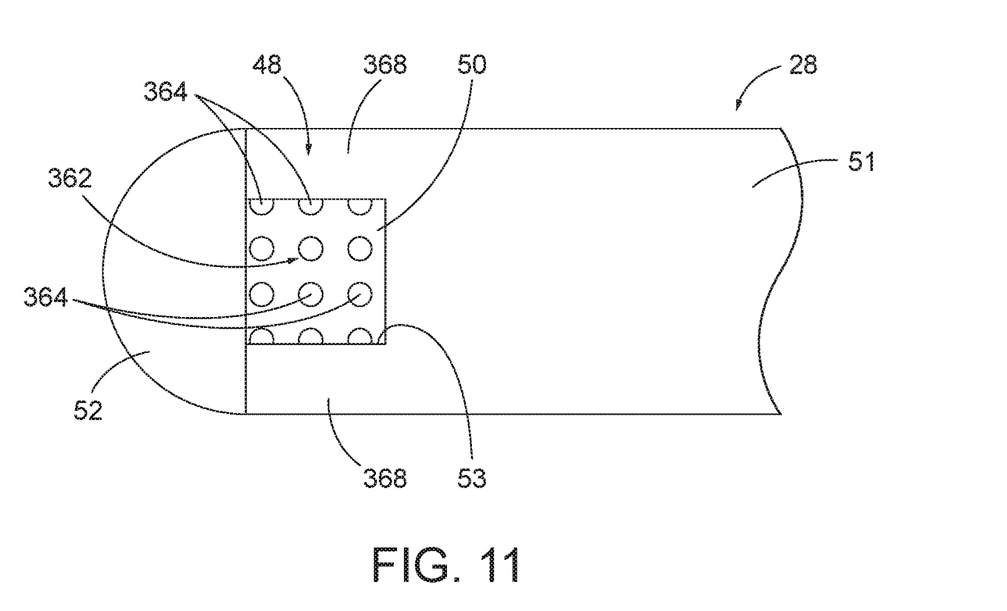
FIG. 11 depicts an enlarged front side elevational view of the shaft of FIG. 10.
Figure 12:
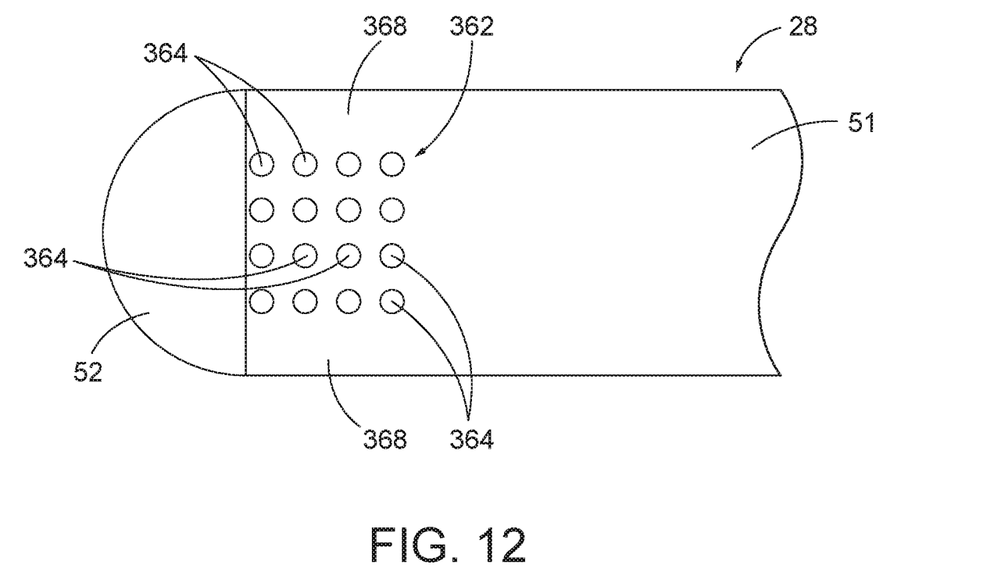
FIG. 12 depicts an enlarged rear side elevational view of the shaft of FIG. 10.

With respect to FIGS. 10-12, aspiration vent (362) more particularly includes a plurality of vent openings (364) that are positioned opposite from shaft window opening (50) and extend through tubular sidewall (51) of shaft (28). Vent openings (364) of the present example are arranged in a series of rows and a series of columns. As oriented in FIGS. 11-12, vent openings (364) are circular bores arranged in five rows and four columns, although it will be appreciated that vent openings (364) may be alternatively sized and positioned. The columns of vent openings (364) are offset from shaft window opening (50) to define a radial sidewall portion (368) on each radial side of shaft window opening (50). Each radial sidewall portion (368) is generally larger than cutting window opening (54) through cutting member (30) such that alignment of radial sidewall portion (368) blocks airflow therethrough and fluidly disconnects the environment from lumen (46).

Figure 13A:
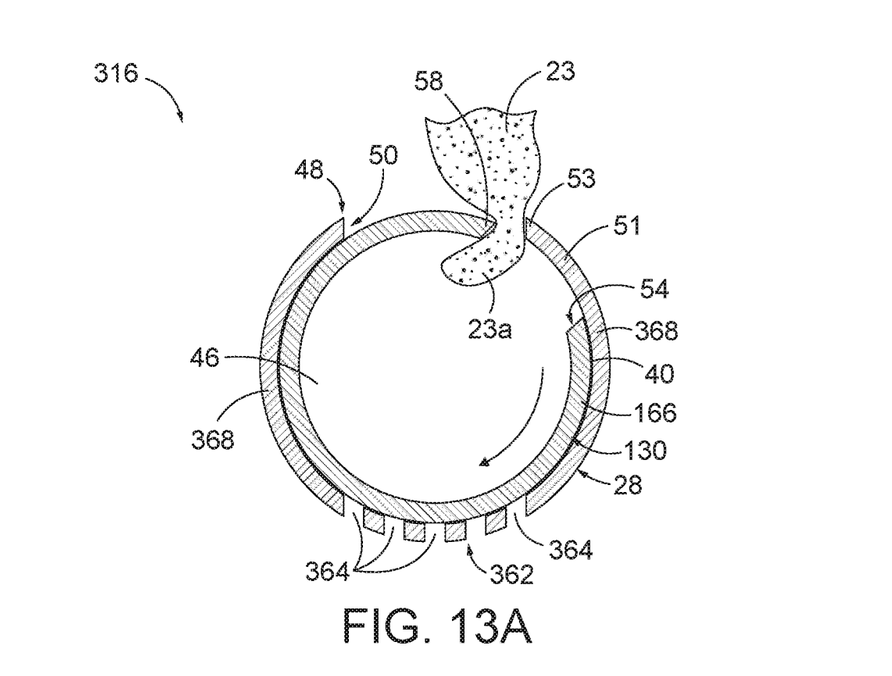
FIG. 13A depicts a sectional view of the shaft assembly of FIG. 10 taken transversely through the centerline and the aspiration vent, with various components hidden for clarity, illustrating a tissue extending through a window opening and against a cutting edge.
Figure 13B:
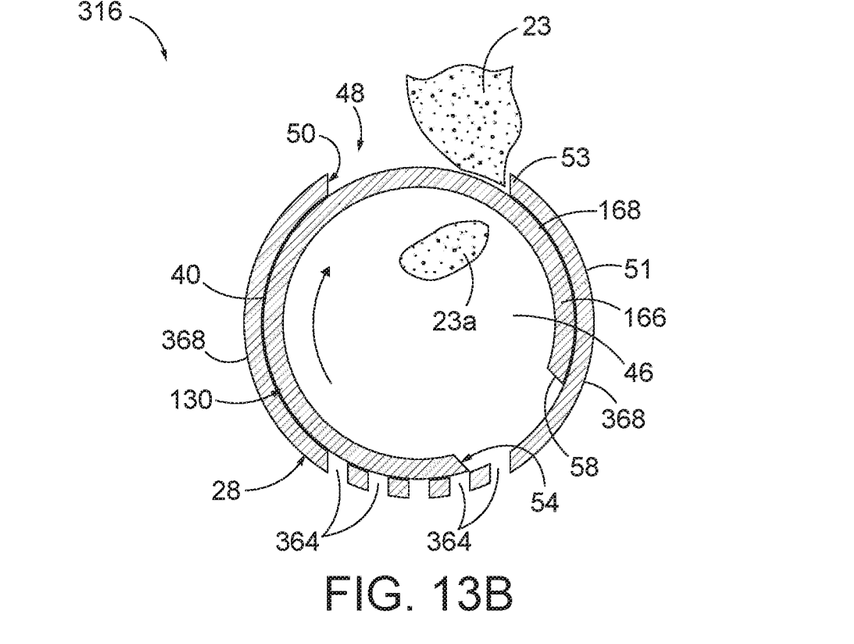
FIG. 13B depicts the sectional view of the shaft assembly similar to FIG. 13A, but showing the cutting edge rotating relative to the window opening and cutting the tissue while maintaining a vacuum for proximally clearing the tissue from the shaft assembly.

Window opening (50) and vent openings (364) respectively cooperate with cutting window opening (54) through cutting member (30) to intermittently suction stalled airflow and a vent airflow along lumen (46) as shown in FIGS. 13A-13B. To this end, cutting edge (58) cuts tissue portion (23A) and vacuum source (22) (see FIG. 1) suctions tissue (23) into cutting window opening (54) as discussed above with respect to FIG. 4A and as illustrated in FIG. 13A in the present example. Further cyclical rotation of cutting member (130) within shaft (28) causes vent openings (364) to align with cutting window opening (54) through another range of cyclical rotational positions for fluid communication therethrough. Vent openings (364) and cutting window opening (54) thus fluidly connect lumen (46) to the environment as aspiration vent (362) such that vacuum source (22) withdraws the vent airflow therethrough proximally along lumen (46). The vent airflow continues until each vent opening (364) rotates past cutting window opening (54) beyond alignment to fluidly disconnect lumen (46) from the environment. Thereby, vent airflow through lumen (46) essentially terminates as radial sidewall portion (368) covers cutting window opening (54) such that vacuum source (22) (see FIG. 1) accumulates the vacuum within lumen (46) and stalls airflow as discussed above.

In use, with respect to FIG. 13A, tissue portion (23a) is cut from tissue (23) between front cutting edge (58) and dull edge (53) as cutting window opening (54) rotatably passes by shaft window opening (50) and stalls airflow within lumen (46). Cutting member (30) continues to cyclically rotate with tissue portion (23a) within lumen (46), such as shown in FIG. 13B. As vent openings (364) fluidly connect to cutting window opening (54) to collectively define aspiration vent (362), vacuum source (22) (see FIG. 1) draws vent airflow therethrough from the environment and into lumen (46). Vent airflow from aspiration vent (362) proximally flows toward suction port (20) (see FIG. 1) and, in turn, similarly urges tissue portion (23a) within lumen (46) away from cutting edge (58) and toward suction port (20). Vent airflow continues to proximally urge tissue portion (23a) clear of cutting edge (58) until vent openings (364) rotate past cutting window opening (54) to again stall airflow as shown again in FIG. 13A. The cyclical rotation of cutting member (30) within shaft (28) repeats the above cutting of tissue (23) and suctioning of intermittent window and vent airflows to effectively clear cutting edge (58) of tissue portions (23a).

Figure 14:
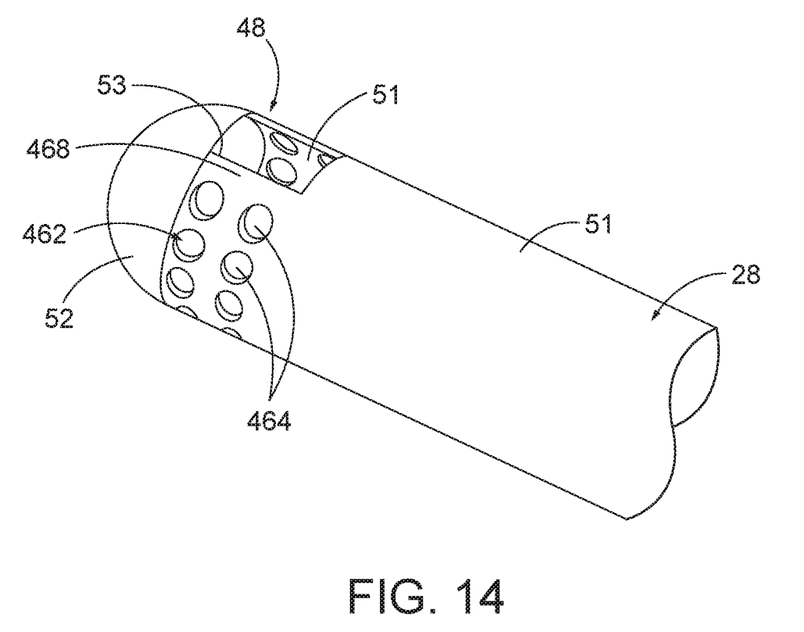
FIG. 14 depicts an exploded perspective fragmentary view of a shaft similar to the shaft of FIG. 10, but having a fourth exemplary aspiration vent.

FIG. 14 illustrates shaft (28) with a fourth exemplary aspiration vent (462) having a plurality of vent openings (464). Aspiration vent (462) is similar to aspiration vent (362) (see FIG. 10) discussed above, but with vent openings (464) sized and positioned such that alternative radial sidewall portions (468) are generally smaller than cutting window opening (54). Thus, at least one of shaft window opening (50) and vent openings (464) are always in fluid communication with cutting window opening (54) for continuous window and/or vent airflows during cyclical movement rather than intermittent window and vent airflows as discussed above. Such vent openings (464) are thereby configured to reduce or even prevent, stalled airflow through lumen (46) during use.

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical instrument, comprising: (a) a shaft extending along a longitudinal axis and including: (i) a shaft lumen extending along the longitudinal axis, (ii) a shaft window opening in fluid communication with an environment and the shaft lumen and configured to receive tissue therein from the environment, and (iii) a shaft edge at least partially surrounding the shaft window opening; (b) a cutting member disposed within the shaft lumen and configured to cyclically move from a first position to a second position relative to the shaft, wherein the cutting member includes: (i) a first cutting window opening in fluid communication with the shaft window opening in the first position and configured to receive the tissue therein, (ii) a first cutting edge at least partially surrounding the first cutting window opening and configured to be cyclically moved within the shaft lumen adjacent to the shaft edge for cutting a tissue portion from the tissue between the first cutting edge and the shaft edge, and (iii) a suction lumen extending along the longitudinal axis in fluid communication with the first cutting window opening and configured to connect to a vacuum source, wherein the suction lumen is in fluid communication with the first cutting window opening and the shaft window opening in the first position; and (c) an aspiration vent extending through at least one of the shaft or the cutting member, wherein the aspiration vent with the cutting member in the second position is in fluid communication with the environment and the suction lumen and configured to suction an airflow from the environment through the aspiration vent and along the suction lumen for further urging the tissue portion away from the first cutting edge and along the suction lumen.

EXAMPLE 2

The surgical instrument of Example 1, wherein the aspiration vent extends through the cutting member and is in fluid communication with the suction lumen.

EXAMPLE 3

The surgical instrument of Example 2, wherein the cutting member further includes: (i) a second cutting window opening in fluid communication with the shaft window opening in the second position and the suction lumen and configured to receive the tissue therein, and (ii) a second cutting edge at least partially surrounding the second cutting window opening and configured to be cyclically moved within the shaft lumen adjacent to the shaft edge for cutting another tissue portion from the tissue between the second cutting edge and the shaft edge, wherein the suction lumen is in fluid communication with the second cutting window opening and the shaft window opening in the second position.

EXAMPLE 4

The surgical instrument of Example 3, wherein the second cutting window opening is positioned radially opposite from the first cutting window opening about the longitudinal axis.

EXAMPLE 5

The surgical instrument of Example 4, wherein the cyclical movement includes rotation of the cutting member relative to the shaft a first rotational direction about the longitudinal axis.

EXAMPLE 6

The surgical instrument of any one or more of Examples 2 through 5, wherein the aspiration vent includes a plurality of vent openings, and wherein the plurality of vent openings are angularly positioned about the cutting member to extend therethrough to fluidly communicate with the suction lumen.

EXAMPLE 7

The surgical instrument of Example 6, wherein at least one of the plurality of vent openings or the first cutting window opening is in continuous fluid communication with the shaft window opening and the suction lumen through cyclical movement of the cutting member relative to the shaft.

EXAMPLE 8

The surgical instrument of any one or more of Examples 1 through 7, wherein the aspiration vent extends through the shaft and is configured to be in fluid communication with the suction lumen via the first cutting window opening.

EXAMPLE 9

The surgical instrument of Example 8, wherein the aspiration vent includes a plurality of vent openings, and wherein the plurality of vent openings are angularly positioned about the shaft to extend therethrough to fluidly communicate with the suction lumen via the first cutting window opening.

EXAMPLE 10

The surgical instrument of Example 9, wherein at least one of the plurality of vent openings or the shaft window opening is in continuous fluid communication with the first cutting window opening and the suction lumen throughout cyclical movement of the cutting member relative to the shaft.

EXAMPLE 11

The surgical instrument of any one or more of Examples 1 through 10, wherein the cyclical movement includes rotation of the cutting member relative to the shaft a first rotational direction about the longitudinal axis.

EXAMPLE 12

The surgical instrument of any one or more of Examples 1 through 11, wherein the aspiration vent and the first cutting window opening are in intermittent fluid communication with the shaft window opening and the suction lumen through cyclical movement of the cutting member relative to the shaft.

EXAMPLE 13

The surgical instrument of any one or more of Examples 1 through 12, wherein at least one of the aspiration vent or the first cutting window opening is in continuous fluid communication with the shaft window opening and the suction lumen through cyclical movement of the cutting member relative to the shaft.

EXAMPLE 14

The surgical instrument of any one or more of Examples 1 through 13, wherein the aspiration vent and the shaft window opening are in intermittent fluid communication with the first cutting window opening and the suction lumen throughout cyclical movement of the cutting member relative to the shaft.

EXAMPLE 15

The surgical instrument of any one or more of Examples 1 through 14, wherein at least one of the aspiration vent or the shaft window opening is in continuous fluid communication with the first cutting window opening and the suction lumen throughout cyclical movement of the cutting member relative to the shaft.

EXAMPLE 16

A surgical instrument, comprising: (a) a handle assembly including: (i) a body, (ii) a suction port configured to connected to a vacuum source, and (iii) a motorized drive assembly; and (b) a shaft assembly extending distally from the handle assembly and including: (i) a shaft extending along a longitudinal axis having: (A) a shaft lumen extending along the longitudinal axis, (B) a shaft window opening in fluid communication with an environment and the shaft lumen and configured to receive a tissue therein from the environment, and (C) a shaft edge at least partially surrounding the shaft window opening, (ii) a cutting member disposed within the shaft lumen and connected to the motorized drive assembly, wherein the motorized drive assembly is configured to cyclically move the cutting member from a first position to a second position relative to the shaft, wherein the cutting member includes: (A) a first cutting window opening in fluid communication with the shaft window opening in the first position and configured to receive the tissue therein, (B) a cutting edge at least partially surrounding the first cutting window opening and configured to be cyclically moved within the shaft lumen adjacent to the shaft edge for cutting a tissue portion from the tissue between the cutting edge and the shaft edge, and (C) a suction lumen extending along the longitudinal axis in fluid communication with the first cutting window opening and fluidly connected to the suction port, wherein the suction lumen is in fluid communication with the first cutting window opening and the shaft window opening in the first position, and (iii) an aspiration vent extending through at least one of the shaft or the cutting member, wherein the aspiration vent with the cutting member in the second position is in fluid communication with the environment and the suction lumen and configured to suction an airflow from the environment through the aspiration vent and along the suction lumen for further urging the tissue portion away from the cutting edge and along the suction lumen.

EXAMPLE 17

The surgical instrument of Example 16, wherein the cyclical movement includes rotation of the cutting member relative to the shaft a first rotational direction about the longitudinal axis.

EXAMPLE 18

The surgical instrument of Example 17, wherein the aspiration vent extends through the cutting member and is in fluid communication with the suction lumen.

EXAMPLE 19

The surgical instrument of Example 18, wherein the aspiration vent includes a plurality of vent openings, and wherein the plurality of vent openings are angularly positioned about the cutting member to extend therethrough to fluidly communicate with the suction lumen.

EXAMPLE 20

A method of removing a tissue portion with a surgical instrument, wherein the surgical instrument has a shaft, a cutting member, and an aspiration vent, wherein the shaft extends along a longitudinal axis and includes a shaft window opening in fluid communication with an environment, wherein the cutting member is disposed within the shaft and is configured to cyclically move from a first position to a second position relative to the shaft, wherein the cutting member includes a cutting edge and a suction lumen extending along the longitudinal axis, wherein the suction lumen is operatively connected to a vacuum source, and wherein the aspiration vent extends through at least one of the shaft or the cutting member, the method comprising: (a) cutting the tissue portion from a mass of tissue with the cutting edge of the cutting member in a first position; (b) cyclically moving the cutting member relative to the shaft from the first position to the second position; (c) suctioning an airflow from the environment through an aspiration vent into the suction lumen in the second position; and (d) urging the tissue portion away from the cutting edge with the airflow.

III. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a shaft extending along a longitudinal axis and including:
      (i) a shaft lumen extending along the longitudinal axis,
      (ii) a shaft window opening in fluid communication with an environment and the shaft lumen and configured to receive tissue therein from the environment, and
      (iii) a shaft edge at least partially surrounding the shaft window opening;
   (b) a cutting member disposed within the shaft lumen and configured to cyclically move from a first position to a second position relative to the shaft, wherein the cutting member includes:
      (i) a first cutting window opening in fluid communication with the shaft window opening in the first position and configured to receive the tissue therein,
      (ii) a first cutting edge at least partially surrounding the first cutting window opening and configured to be cyclically moved within the shaft lumen adjacent to the shaft edge for cutting a tissue portion from the tissue between the first cutting edge and the shaft edge,
      (iii) a suction lumen extending along the longitudinal axis in fluid communication with the first cutting window opening and configured to connect to a vacuum source, wherein the suction lumen is in fluid communication with the first cutting window opening and the shaft window opening in the first position, and (iv) first and second sidewall portions on each radial side of the first cutting window, wherein at least one of the first and the second sidewall portions is larger than the shaft window opening, wherein alignment of the at least one of the first and the second sidewall portions with the shaft window opening fluidly disconnects the environment from the suction lumen; and (c) an aspiration vent extending through the cutting member, wherein the aspiration vent with the cutting member in the second position is in fluid communication with the environment and the suction lumen and configured to suction an airflow from the environment through the aspiration vent and along the suction lumen for further urging the tissue portion away from the first cutting edge and along the suction lumen.

2. The surgical instrument of claim 1, wherein the cutting member further includes:

(i) a second cutting window opening in fluid communication with the shaft window opening in the second position and the suction lumen and configured to receive the tissue therein, and (ii) a second cutting edge at least partially surrounding the second cutting window opening and configured to be cyclically moved within the shaft lumen adjacent to the shaft edge for cutting another tissue portion from the tissue between the second cutting edge and the shaft edge, wherein the suction lumen is in fluid communication with the second cutting window opening and the shaft window opening in the second position.

3. The surgical instrument of claim 2, wherein the second cutting window opening is positioned radially opposite from the first cutting window opening about the longitudinal axis.

4. The surgical instrument of claim 3, wherein the cyclical movement includes rotation of the cutting member relative to the shaft a first rotational direction about the longitudinal axis.

5. The surgical instrument of claim 1, wherein the aspiration vent includes a plurality of vent openings, and wherein the plurality of vent openings are angularly positioned about the cutting member to extend therethrough to fluidly communicate with the suction lumen.

6. The surgical instrument of claim 5, wherein at least one of the plurality of vent openings or the first cutting window opening is in continuous fluid communication with the shaft window opening and the suction lumen through cyclical movement of the cutting member relative to the shaft.

7. The surgical instrument of claim 5, wherein the plurality of vent openings includes a pattern of bore holes arranged in a series of rows and columns.

8. The surgical instrument of claim 1, wherein the cyclical movement includes rotation of the cutting member relative to the shaft a first rotational direction about the longitudinal axis.

9. The surgical instrument of claim 1, wherein the aspiration vent and the first cutting window opening are in intermittent fluid communication with the shaft window opening and the suction lumen through cyclical movement of the cutting member relative to the shaft.

10. The surgical instrument of claim 1, wherein at least one of the aspiration vent or the first cutting window opening is in continuous fluid communication with the shaft window opening and the suction lumen through cyclical movement of the cutting member relative to the shaft.

11. The surgical instrument of claim 1, wherein the aspiration vent and the shaft window opening are in intermittent fluid communication with the first cutting window opening and the suction lumen throughout cyclical movement of the cutting member relative to the shaft.

12. The surgical instrument of claim 1, wherein at least one of the aspiration vent or the shaft window opening is in continuous fluid communication with the first cutting window opening and the suction lumen throughout cyclical movement of the cutting member relative to the shaft.

13. The surgical instrument of claim 1, wherein at least one of the first and the second sidewall portion is configured to fluidly disconnect the environment from the suction lumen as the cutting member moves from the first position to the second position relative to the shaft.

14. The surgical instrument of claim 1, wherein the cyclical movement includes oscillation of the cutting member relative to the shaft a first rotational direction about the longitudinal axis and a second rotational direction about the longitudinal axis.

15. A surgical instrument, comprising:

(a) a handle assembly including:
  (i) a body,
  (ii) a suction port configured to be connected to a vacuum source, and
  (iii) a motorized drive assembly; and (b) a shaft assembly extending distally from the handle assembly and including:
  (i) a shaft extending along a longitudinal axis having:
    (A) a shaft lumen extending along the longitudinal axis,
    (B) a shaft window opening in fluid communication with an environment and the shaft lumen and configured to receive a tissue therein from the environment, and
    (C) a shaft edge at least partially surrounding the shaft window opening,
  (ii) a cutting member disposed within the shaft lumen and connected to the motorized drive assembly, wherein the motorized drive assembly is configured to cyclically move the cutting member from a first position to a second position relative to the shaft, wherein the cutting member includes:
    (A) a first cutting window opening in fluid communication with the shaft window opening in the first position and configured to receive the tissue therein,
    (B) a cutting edge at least partially surrounding the first cutting window opening and configured to be cyclically moved within the shaft lumen adjacent to the shaft edge for cutting a tissue portion from the tissue between the cutting edge and the shaft edge, and
    (C) a suction lumen extending along the longitudinal axis in fluid communication with the first cutting window opening and fluidly connected to the suction port, wherein the suction lumen is in fluid communication with the first cutting window opening and the shaft window opening in the first position,
    (D) a sidewall portion located on a radial side of the first cutting window, wherein the sidewall portion is larger than the shaft window opening, wherein alignment of the sidewall portion with the shaft window opening fluidly disconnects the environment from the suction lumen, and
  (iii) an aspiration vent extending through the cutting member, wherein the aspiration vent with the cutting member in the second position is in fluid communication with the environment and the suction lumen and configured to suction an airflow from the environment through the aspiration vent and along the suction lumen for further urging the tissue portion away from the cutting edge and along the suction lumen.

16. The surgical instrument of claim 15, wherein the cyclical movement includes rotation of the cutting member relative to the shaft a first rotational direction about the longitudinal axis.

17. The surgical instrument of claim 15, wherein the aspiration vent includes a plurality of vent openings, and wherein the plurality of vent openings are angularly positioned about the cutting member to extend therethrough to fluidly communicate with the suction lumen.

18. The surgical instrument of claim 17, wherein the plurality of vent openings includes a pattern of bore holes arranged in a series of rows and columns.

19. The surgical instrument of claim 15, wherein the sidewall portion is configured to fluidly disconnect the environment from the suction lumen as the cutting member moves from the first position to the second position relative to the shaft.

20. A method of removing a tissue portion with a surgical instrument, wherein the surgical instrument has a shaft and a cutting member, wherein the shaft extends along a longitudinal axis and includes a shaft window opening in fluid communication with an environment, wherein the cutting member is disposed within the shaft and is configured to cyclically move from a first position to a second position through an intermediate position relative to the shaft, wherein the cutting member includes a cutting edge, an aspiration vent, a radial sidewall portion positioned between the cutting edge and the aspiration vent, and a suction lumen extending along the longitudinal axis, wherein the suction lumen is operatively connected to a vacuum source, the method comprising:

(a) cutting the tissue portion from a mass of tissue with the cutting edge of the cutting member in the first position;

(b) cyclically moving the cutting member relative to the shaft from the first position to the second position, wherein in the intermediate position between the first position and the second position the radial sidewall portion of the cutting member is configured to fluidly disconnect the environment from the suction lumen;

(c) suctioning an airflow from the environment through the aspiration vent defined by the cutting member into the suction lumen in the second position; and (d) urging the tissue portion away from the cutting edge with the airflow.

* * * * *